United States Patent
Wieczorek et al.

(10) Patent No.: US 7,989,771 B2
(45) Date of Patent: Aug. 2, 2011

(54) PINHOLE SPECT CAMERA WITH PLURAL DETECTOR HEADS

(75) Inventors: Herfried K. Wieczorek, Aachen (DE);
Rolf D. Bippus, Lemiers (NL); Henrik Botterweck, Aachen (DE); Andreas Goedicke, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 327 days.

(21) Appl. No.: 11/913,847

(22) PCT Filed: May 1, 2006

(86) PCT No.: PCT/IB2006/051355
§ 371 (c)(1),
(2), (4) Date: Nov. 8, 2007

(87) PCT Pub. No.: WO2006/120605
PCT Pub. Date: Nov. 16, 2006

(65) Prior Publication Data
US 2010/0001190 A1    Jan. 7, 2010

Related U.S. Application Data

(60) Provisional application No. 60/681,113, filed on May 13, 2005.

(51) Int. Cl.
*G01T 1/161* (2006.01)
(52) U.S. Cl. .................................................. 250/363.1
(58) Field of Classification Search ................. 250/363.1
See application file for complete search history.

(56) References Cited

U.S. PATENT DOCUMENTS

| | | | |
|---|---|---|---|
| 3,107,276 A * | 10/1963 | Cohen | 348/162 |
| 4,058,727 A | 11/1977 | Stout | |
| 5,032,728 A | 7/1991 | Chang et al. | |
| 5,245,191 A | 9/1993 | Barber et al. | |
| 7,166,846 B2 * | 1/2007 | Engdahl et al. | 250/363.1 |
| 2004/0232348 A1 | 11/2004 | Beekman | |
| 2004/0239941 A1 | 12/2004 | Schramm et al. | |

FOREIGN PATENT DOCUMENTS

| | | |
|---|---|---|
| DE | 2415424 A1 | 10/1975 |
| WO | 02093195 A2 | 11/2002 |
| WO | 03021292 A2 | 3/2003 |

OTHER PUBLICATIONS

Brasse, D., et al.; Development of a High Resolution SPECT System Dedicated to Small Animal Imaging; 2004; IEEE Nuclear Science Symposium Conference; Record (Rome) pp. 3868-3871.
Furenlid, et al.; FastSPECT II: A second-generation high-resolution dynamic SPECT imager; 2004; IEEE; Trans. Nucl. Sci. vol. 51, pp. 631-635.

* cited by examiner

*Primary Examiner* — Constantine Hannaher

(57) ABSTRACT

An imaging system (10) includes at least one radiation detector unit (16) disposed adjacent a field of view (20) to detect and measure radiation from the field of view (20). The detector unit (16) includes multiple detection modules (18) which each detects radiation from a prespecified region of the field of view (20), each region being a fraction of the field of view. One or more pinholes (52) are associated with the detector unit (16). Each pinhole (52) receives radiation from the prespecified region of the field of view (20) and transmits radiation to one or more associated detection modules (18).

20 Claims, 4 Drawing Sheets

PINHOLE SPECT CAMERA WITH PLURAL DETECTOR HEADS

CROSS REFERENCE TO RELATED APPLICATIONS

This application is a national state entry (35USC371) of PCT/IB2006/051355 filed May 1, 2006 and claims the benefit (35 USC 119) of U.S. provisional application Ser. No. 60,681,113 filed May 13, 2005.

The present invention relates to the diagnostic imaging systems and methods. It finds particular application in conjunction with the Single Photon Emission Tomography (SPECT) systems and will be described with particular reference thereto. It will be appreciated that the invention is also applicable to other imaging systems such as Positron Emission Tomography systems (PET) and the like.

Nuclear medicine imaging employs a source of radioactivity to image a patient. Typically, a radiopharmaceutical is injected into the patient. Radiopharmaceutical compounds contain a radioisotope that undergoes gamma-ray decay at a predictable rate and characteristic energy. One or more radiation detectors are placed adjacent to the patient to monitor and record emitted radiation. Sometimes, the detector is rotated or indexed around the patient to monitor the emitted radiation from a plurality of directions. Based on information such as detected position and energy, the radiopharmaceutical distribution in the body is determined and an image of the distribution is reconstructed to study the circulatory system, radiopharmaceutical uptake in selected organs or tissue, and the like.

Typically, in SPECT imaging, a collimator is positioned in front of the detector to control the direction of radiation and angular spread from which each element of the detector can receive the radiation. The collimator typically includes plates or septa disposed parallel to each other. However, such collimator introduces shadowing of individual detector elements or pixels. The problem is most prominent when the radiopharmaceuticals which produce high energy photons, such as In-111, Ga-67, or I-131, are used for imaging. High-energy photons need thicker septa to be effective rendering parallel collimation impractical.

One solution is to use a pinhole collimator. Typically, the pinhole collimator is positioned some distance from both the object to be examined and from the detectors, e.g. very close to the field of view. The pinhole functions, analogous to a primitive pinhole photograph camera, act like a lens to "focus" the entire field of view onto the detector. Such pinholes, closely positioned to the field of view, have a relatively large opening angle to cover the entire field of view. The low number of pinholes and the large opening angle, in combination with the $\cos^3 \theta$-dependence of detector efficiency for non-perpendicular detector geometry, which results in a low average efficiency, account for a low system efficiency. For a larger number of pinholes, the pinhole cylinder is positioned further away from the field of view and the detector area is increased. A cylindrical arrangement of many pinholes is achievable if the distance from the pinhole cylinder to the center of the field-of-view (FOV) is larger than the radius of the FOV itself. The system efficiency increases with an increased number of pinholes, but the detector perimeter and overall area are significantly increased which becomes expensive.

The present invention provides a new and improved imaging apparatus and method which overcomes the above-referenced problems and others.

In accordance with one aspect of the present invention, an imaging system is disclosed. At least one radiation detector unit is disposed adjacent a field of view to detect and measure radiation from the field of view. The detector unit includes multiple detection modules. Each detection module detects radiation from a prespecified region of the field of view, each region being a fraction of the field of view. One or more pinholes are associated with the detector unit. Each pinhole receives radiation from the prespecified region of the field of view and transmits radiation to one or more associated detection modules.

In accordance with another aspect, a method of imaging is disclosed. Radiation that has passed through one or more pinholes from a subject disposed in a field of view is detected with multiple detection modules, each detection module detecting radiation from a prespecified region of the field of view, each region being a fraction of the field of view.

In accordance with another aspect, a diagnostic imaging apparatus is disclosed. A gantry assembly supports at least one detector unit at a plurality of locations around a field of view. Each detector unit includes a plurality of two dimensional detector modules, and a collimator plate which defines one or more apertures. A number of apertures is equal to or less than a number of detector modules. The detector modules are positioned relative to the collimator plate such that each detector receives radiation through single one of the apertures and from only a fraction of the field of view. A reconstruction processor reconstructs signals from the detector modules into an image representation.

One advantage of the present invention resides in increased system efficiency.

Another advantage resides in near field imaging for large fields of view.

Another advantage resides in maintaining the detector area.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 3B:
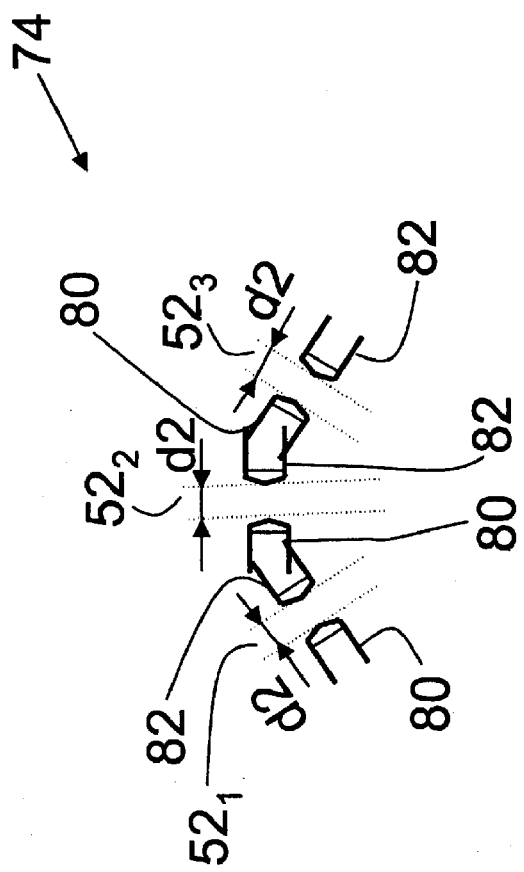
Figure 3A:
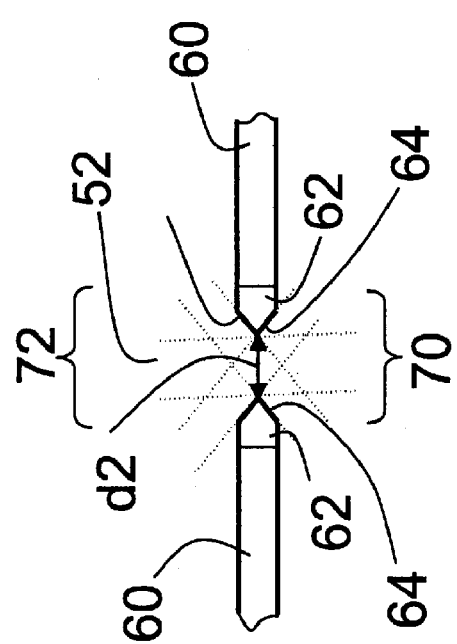

FIG. 3A diagrammatically shows geometry of a single pinhole collimator; and

FIG. 3B diagrammatically shows geometry of a triple hole pinhole collimator.

Figure 1:
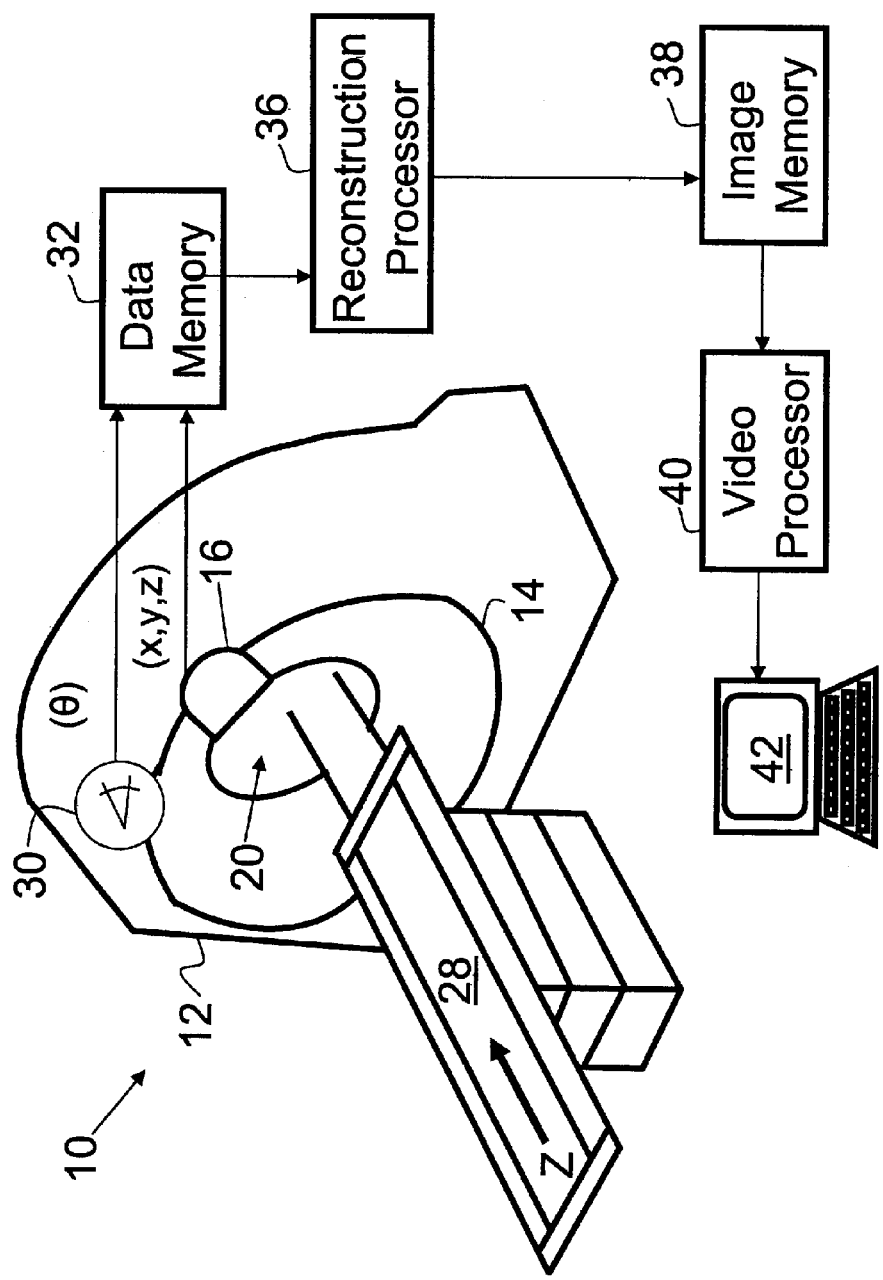
FIG. 1 is a diagrammatic illustration of an imaging system.

With reference to FIG. 1, a nuclear imaging system 10 typically includes a stationary gantry 12 that supports a rotatable gantry 14. One or more detector units 16, each including multiple detection heads or cameras 18 are carried by the rotatable gantry 14 to detect radiation events emanating from a region of interest or examination region or field of view (FOV) 20. The detection units 16 are arranged generally circumferentially about the field of view 20.

Typically, an object to be imaged is injected with one or more radiopharmaceuticals or radioisotopes and placed in the examination region 20 supported by a couch 28. A few examples of such isotopes include Tc-99m, I-131, Ga-67, and In-111. The presence of the radiopharmaceuticals within the object produces emission radiation from the object. Radiation is detected by the detection units 16 which are able to be angularly indexed or rotated around the examination region 20 to collect the projection emission data at one or more selected projection directions. The projection emission data, e.g. the location (x, y), energy (z), and an angular position (θ) of each detection unit 16 around the examination region 20 (e.g., obtained from an angular position resolver 30) are stored in a data memory 32. A reconstruction processor 36 processes the event and detector orientation data from the data memory 32 into a volumetric image representation. The image representation is stored in an image memory 38 for manipulation by a video processor 40 and display on an image display 42 such as a video monitor, printer, or the like.

Figure 2A:
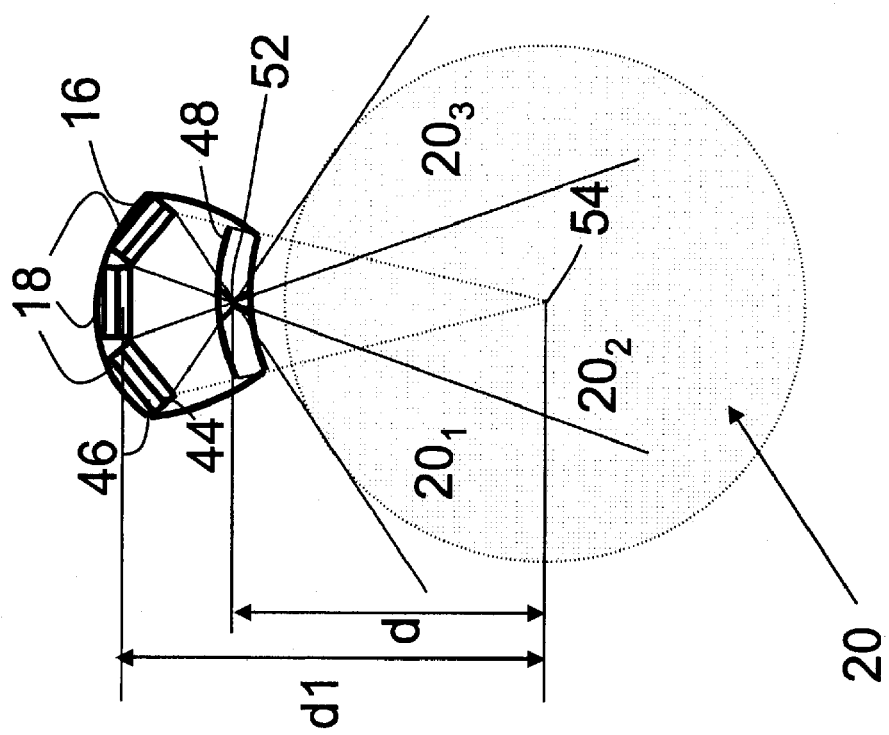
FIG. 2A is a diagrammatic illustration of one arrangement of detection heads and a pinhole collimator.
Figure 2B:
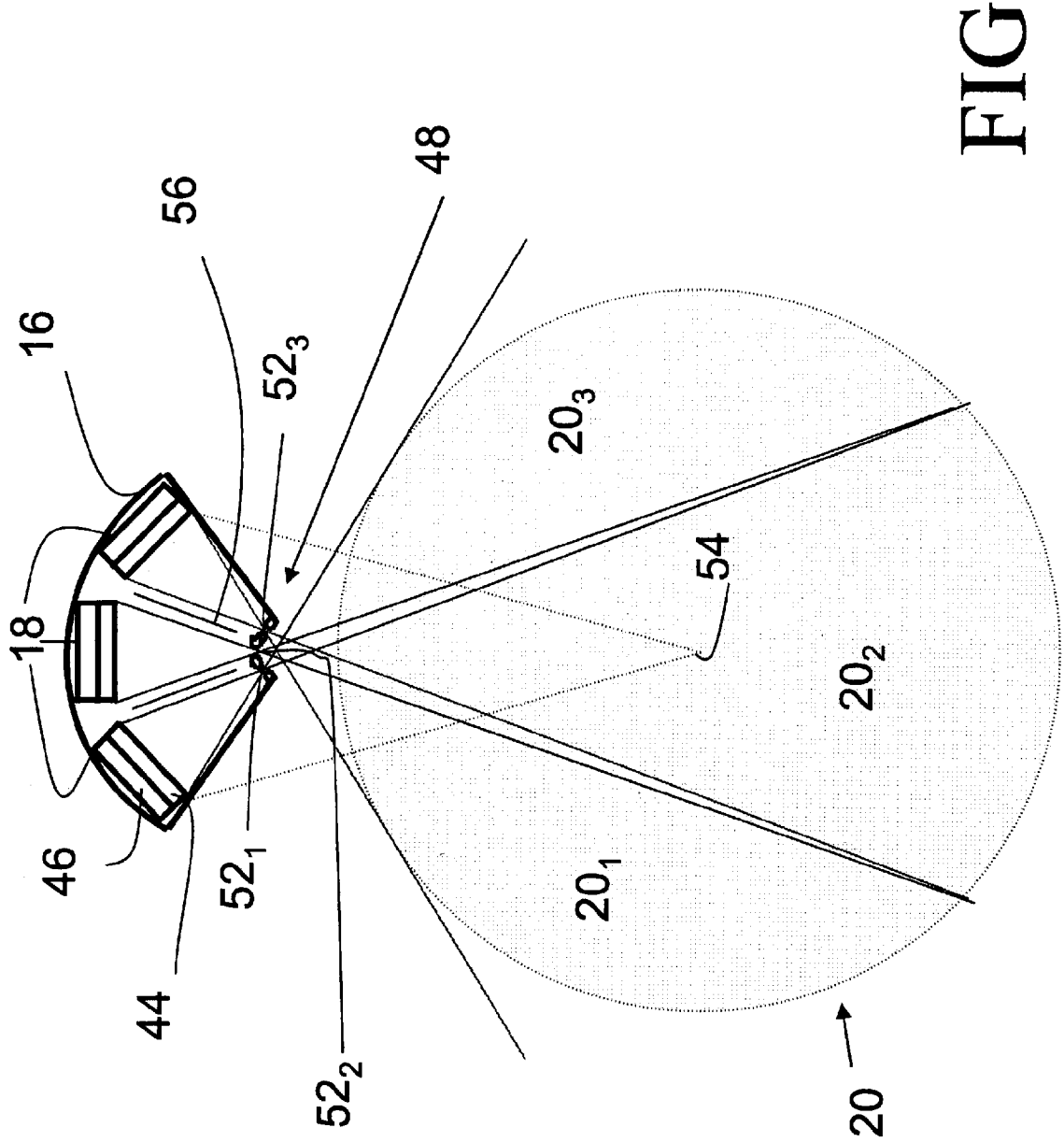
FIG. 2B is a diagrammatic illustration of another arrangement of detection heads and a pinhole collimator.

With continuing reference to FIG. 1 and further reference to FIGS. 2A and 2B, the detection heads 18 of each detector unit 16 are arranged on a generally hemispherical or cylindrical surface. Such heads are preferably relatively small, e.g. about a 20×20 cm active area. Each detection head 18 includes two-dimensional arrays of detector elements or detector 44 such as a scintillator and light sensitive elements, e.g. photomultiplier tubes, photodiodes, and the like. Direct photon to electrical converters, such as CZT elements, are also contemplated. Each head 18 includes circuitry 46 for converting each radiation response into a digital signal indicative of its location (x, y) on the detector face and its energy (z). The location of an event on the detector 44 is resolved and/or determined in a two dimensional (2D) Cartesian coordinate system with nominally termed x and y coordinates. However, other coordinate systems are contemplated. In each detector unit 16, a collimator 48 controls the direction and angular spread, from which each element of the detector 44 can receive radiation, i.e., the detector 44 can receive radiation only along known rays. Thus, the determined location on the detector 44 at which radiation is detected, the position of the detector within the detection unit 16, and the angular position of the detector unit define the nominal ray along which each radiation event occurred. As discussed below, in one embodiment, the collimator 48 employs a pinhole collimation. In another embodiment, the collimator 48 employs a slat-slit or fan-slit collimation in which an axial pinhole width slit has collimator slats transverse to the axial direction Z. The slat-slit and fan-slit collimation techniques are known in the art.

The collimator 48 of each detector unit 16 includes one or more pinholes 52. In one embodiment, the pinhole 52 is a real pinhole and provides a true 3D pinhole collimation. In another embodiment, the pinhole 52 is a slit and provides the pinhole collimation in the direction transverse to the axial direction Z. In the axial direction Z, the collimation is the slat collimation, e.g. the pinhole slit extends in the Z direction and the slats extend circumferentially. Additional collimation can be provided by slats or fan beam collimation known in the art. In one embodiment, a single ring of the detector units 16 is rotated on the rotatable gantry 14.

In a pinhole embodiment, the detectors 44 are positioned along a piecewise continuous arc, e.g. the three detectors illustrated in FIG. 2A. In a pinhole slit embodiment in which the slit is longer axially than the detector 44, a corresponding plurality of detectors is arranged axially along a piecewise continuous cylinder. In a true pinhole collimator, the detectors can be positioned along a piecewise continuous hemispherical segment, e.g. with a cross-section as illustrated in FIG. 2A in both the axial and transverse directions.

The size of pinhole 52 and the geometry between the field of view and the detector are selected to define a relatively small viewing angle $a_{fan}$, for example, less than 40°. In one embodiment, a ratio between a pinhole to the center of the field of view distance d to a camera to the center of the field of view distance d1 is equal to or greater than 2 to 3, i.e., d:d1≧2:3. The collimator 48 with the detector unit 16 is displaced from a center 54 of the field of view 20 and closer to the detection heads 18 to improve efficiency of the detector unit 16.

With continuing reference to FIG. 2A, the illustrated cameras 18 of the detector unit 16 are associated with the single pinhole 52. The field of view 20 is split into equal transverse portions $20_1$, $20_2$, $20_3$ such that each camera 18 views an equal limited portion of the field of view 20. In the exemplary embodiment illustrated in FIG. 2A, each of the three cameras 18 views ⅓ of the field of view. If nine cameras are mounted in the detector unit 16 on a hemispherical surface, each camera views about ⅑th of the field of view. This avoids small angles of incidence and results in an increased system efficiency as discussed below.

With reference again to FIG. 2B, each illustrated camera 18 of the detector unit 16 is associated with an individual pinhole $52_1$, $52_2$, $52_3$. The distances between the pinholes are selected for each pinhole $52_1$, $52_2$, $52_3$ to view the same field of view as in FIG. 2A, e.g. one third of the field of view 20. As discussed below in conjunction with FIG. 3A, the significant thickness of the structure in which the pinhole is defined tends to cause the side cameras to see a smaller effective pinhole than the center camera. Each camera 18 of the FIG. 2B has same spatial resolution. Shields or scatter plates 56 are preferably installed between the pinholes $52_1$, $52_2$, $52_3$ to channel radiation into an appropriate pinhole and prevent radiation transmitted by a "correct" pinhole to reach a disassociated detection head. Of course, it is also contemplated that other number of pinholes can be used such as, for example, two pinholes.

With reference to Table 1 below, the parameters of three different multi-pinhole geometries are calculated. For simplicity of calculation the pinhole concept geometry is calculated only in the Z direction similar to the geometry applied in the slat-slit and fan beam-slit collimation concepts, as discussed above. The field of view in these examples is equal to 100 mm diameter and imaged by 8, 12 or 16 pinholes. A pinhole-to-center of the FOV distance d is respectively equal to 60, 70 and 80 mm. As discussed above, in a traditional concept, in a system which employs large detectors, the pinhole is positioned near the FOV (d=60 mm), the opening angle $a_{fan}$ of the pinhole has to be large (113°) to cover the entire FOV. Only about eight pinholes, or alternatively, slits can be arranged circumferentially around the field of view. The low number of detectors on the cylinder and the large opening angle of the pinholes result in a low average efficiency accounting for the $\cos^3 \theta$-dependence for non-perpendicular detector geometry. As a result, the system efficiency is limited. Assuming a slat-slit geometry in which slats are 0.15 mm slat thick, the system efficiency is equal to 20.6 cps/MBq.

As in shown in Table 1, when the distance d from the pinholes to the center of the FOV is increased to respectively 70 mm and 80 mm, 12 or 16 pinholes can be arranged around the circumference. The system efficiency is increased respectively to 28.8 cps/MBq and 32.8 cps/MBq. The trade off of the increased system efficiency, however, is significant increase in the detector perimeter and detector area.

The last line in Table 1 shows data for a system which employs twelve triple detector units 16 each including three detection heads 18. The distance d from the pinhole 52 to the center 54 of the field of view is equal to 60 mm, the opening angle $a_{fan}$ of the pinhole is small, e.g. is equal to 37.6°, and the detector perimeter is kept small, e.g. equal to 490 mm. However, the system efficiency is increased to 53.0 cps/MBq.

TABLE 1

|  | Pinhole-center FOV distance, d | Detector perimeter | Opening angle, $a_{fan}$ | Module efficiency | System efficiency |
|---|---|---|---|---|---|
| 8 pinholes | 60 mm | 482 mm | 113°/0.55 | 2.58 | 20.6 |
| 12 pinholes | 70 mm | 572 mm | 91.2°/0.70 | 2.40 | 28.8 |
| 16 pinholes | 80 mm | 683 mm | 77.4°/0.78 | 2.05 | 32.8 |
| 12 triple units | 60 mm | 490 mm | 37.6°/0.95 | 4.41 | 53.0 |

With reference to FIGS. 3A and 3B, the collimator 48 includes plates 60 which extend in the axial direction Z. The plates 60 are manufactured from tungsten or other appropriate material. The pinholes 52 are machined into a blocks or discs 62 of gold, or other appropriate material to form opposing pinhole edges 64 which define a pinhole opening d2. The blocks 62 with the pinholes 52 are installed into recesses (not shown) provided in the plates 60. In one embodiment, the pinhole discs 62 are fastened by retaining rings and can be exchanged if alternative aperture sizes are required. The physical dimension of the opening or aperture d2 of the pinhole 52 is preferably small and depends on the spatial resolution to be achieved for imaging the object. In one embodiment, the physical dimension d2 of the pinhole 52 is from about 1 mm to about 7 mm. Of course, it is also contemplated that the pinhole 52 can be very small in size, 0.2 mm, to image very small objects with high resolution.

With continuing reference to FIG. 3A and reference again to FIG. 2A, the single pinhole 52 has geometry in which edges 64 of the pinhole 52 are shaped in a shape of a funnel or "V" shape from a first or photons entering side 70, which is close to the field of view 20, and a second or photons exiting side 72, which is closer to the detection heads, defining first and second funnels which extend in the axial direction Z in the slit collimation geometry. The tapering of the edges enlarges the effective size of the pinhole as viewed by the side cameras relative to the center camera as illustrated in FIG. 3A. Moreover, the areas of the side cameras nearest the center see a larger effective pinhole than the portions of the side cameras closest to the collimator.

With reference again to FIGS. 2B and 3B, a pinhole arrangement 74 includes three pinholes $52_1$, $52_2$, $52_3$, each pinhole $52_1$, $52_2$, $52_3$ being associated with the detection head 18. The blocks 62 of gold or other material are machined to form edges 64 and define equal apertures d2 of each pinhole $52_1$, $52_2$, $52_3$. The edges 64 can be shaped annularly, triangularly, or in any other appropriate shape to form the aperture d2 of a prespecified size and geometry. Each plate 60 includes pairs of first and second portions 80, 82. Each pair of the first and second portions 80, 82 is positioned parallel to one another and orthogonal to an associated pinhole $52_1$, $52_2$, $52_3$. In this manner, each adjacent pair of first and second portions 80, 82 is positioned angularly in relation to one another. Each camera is disposed centered on and perpendicular to the centerline of its associated pinhole. In this manner, each camera views its portion of the field of view through an aperture of the same effective size. Moreover, the center of the field of view to the camera dimension d1, and the center of the field of view to pinhole distance d are the same for all cameras. Thus, each camera has equal resolution.

Alternatively, it may be advantageous for the cameras to have different resolutions or efficiencies. For example, because the region of primary interest is often near the center of the field of view, it may, for some applications, be advantageous for the center to have higher resolution and/or efficiency. As another alternative, each camera can view different unequal fractions of the field of view. Also, the cameras can view the FOV with different degrees of redundancy. For example, each camera of a two camera detector unit can cover ⅔'s of the FOV, with the center ⅓ double covered. Of course, other numbers of cameras per detector unit are also contemplated.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An imaging system comprising:
   at least one radiation detector unit disposed adjacent a field of view to detect radiation from the field of view, the radiation detector unit including:
   a plurality of detection modules disposed along a curve, each detection module detecting radiation from a prespecified region of the field of view, each region being a fraction of the field of view, and
   a plate which defines a plurality of pinholes, each pinhole receives radiation from the prespecified region of the field of view and channels corresponding radiation to one o of the detection modules, the plate being non-planar.

2. The system as set forth in claim 1, wherein d:d1≧2:3 where d is the distance from each pinhole to a center of the field of view and d1 is a distance from each detector module to the center of the field of view.

3. The system as set forth in claim 2, wherein an opening angle of the pinhole is equal to or less than 40°.

4. The system as set forth in claim 1, wherein the field of view is split into regions and each further including scatter plates extending axially between each corresponding pinhole and detector module and a neighboring corresponding pinhole and detector such that each detection module detects only radiation received through the corresponding pinhole.

5. The system as set forth in claim 1, wherein the plurality of detection modules are disposed on a piecewise hemispherical surface.

6. The system as set forth in claim 1, wherein each pinhole is a slit extending in an axial direction.

7. The system as set forth in claim 1, wherein the regions partially overlap.

8. The system as set forth in claim 1, each of the detector modules are a first common distance from the corresponding pinhole and each pinhole is a second common distance from a center of the field of view.

9. The imaging system as set forth in claim 1, wherein each of the pinholes is defined in one of the plurality of blocks which are installed in openings in the plate.

10. The system as set forth in claim 1, wherein the detector modules view different, unequal fractions of the field of view.

11. An imaging system comprising:
    at least one radiation detector unit disposed adjacent a field of view to detect radiation from the field of view, the at least one detector unit including:
    a plurality of detection modules disposed on one of a piecewise continuous cylindrical and hemispheric surface, each detection module detecting radiation from a prespecified region of the field of view, each region being a fraction of the field of view, and;
    a plate which defines a single pinhole each detection module receiving radiation from the prespecified region of the field of view through the single pinhole, the pinhole being defined between edges of the plate that form two opposing funnels which converge into an aperture, the edges being angled such that an effective size of the pinhole as viewed by side detector modules is larger than the effective size of the pinhole as reviewed by a central one of the detector modules.

12. The system as set forth in claim 11, wherein an opening angle of the pinhole is less than or equal to 40°.

13. The system as set forth in claim 11, wherein the pinhole is defined in a block which is installed in an opening in the plate.

14. The system as set forth in claim 11, wherein the pinhole is a slit extending in an axial direction.

15. The system as set forth in claim 11, wherein each detection module is a two dimensional, planar detector, the detection modules being disposed on a piecewise continuous hemispherical surface segment.

16. A diagnostic imaging apparatus comprising:
a gantry assembly which supports at least one detector unit at a plurality of locations around a field of view, each detector unit including:
a plurality of detector modules disposed on a piecewise continuous hemispherical surface segment, and
a collimator plate which defines at least one aperture, the number of apertures being equal to or fewer than a number of detector modules,
the detector modules being positioned relative to the collimator plate such that each detector receives radiation through only one of the apertures and from only a fraction of the field of view; and
a reconstruction processor which reconstructs signals from the detector modules into an image.

17. The diagnostic imaging apparatus as set forth in claim 16, wherein the collimator plate defines a number of apertures which is equal to the number of detector modules.

18. The diagnostic imaging apparatus as set forth in claim 16, wherein each of the detector modules are a first common distance from a corresponding pinhole and each pinhole is a second common distance from a center of the field of view.

19. The diagnostic imaging apparatus as set forth in claim 16, wherein the collimator plate defines a single aperture defined between edges of the collimator plate that form opposing funnels to receive radiation of the field of view through the single aperture, the edges of the collimator plate being angled such that an effective size of the aperture as viewed by side detector modules is larger than the effective size of the aperture as viewed by a central detector module.

20. The diagnostic imaging apparatus as set forth in claim 16, wherein each detector module at least one of:
has a different resolution;
has a different efficiency;
views a different, unequal fraction of the field of view;
has different degrees of redundancy; and
has the same resolution.

* * * * *